United States Patent
Povazay et al.

(10) Patent No.: US 10,024,741 B2
(45) Date of Patent: Jul. 17, 2018

(54) MEASURING DEVICE AND METHOD FOR ASCERTAINING A PRESSURE MAP

(71) Applicant: EV GROUP E. THALLNER GMBH, St. Florian am Inn (AT)

(72) Inventors: Boris Povazay, Vienna (AT); Antun Peic, Tiefenbach (DE)

(73) Assignee: EV GROUP E. THALLNER GMBH, St. Florian am Inn (AT)

( * ) Notice: Subject to any disclaimer, the term of this patent is extended or adjusted under 35 U.S.C. 154(b) by 59 days.

(21) Appl. No.: 14/894,709

(22) PCT Filed: Jun. 5, 2013

(86) PCT No.: PCT/EP2013/061583
§ 371 (c)(1),
(2) Date: Nov. 30, 2015

(87) PCT Pub. No.: WO2014/194944
PCT Pub. Date: Dec. 11, 2014

(65) Prior Publication Data
US 2016/0103026 A1 Apr. 14, 2016

(51) Int. Cl.
*G01L 1/25* (2006.01)
*G01L 1/24* (2006.01)
(Continued)

(52) U.S. Cl.
CPC .............. *G01L 1/242* (2013.01); *G01L 1/247* (2013.01); *G01L 1/25* (2013.01); *G01L 5/0047* (2013.01);
(Continued)

(58) Field of Classification Search
CPC ......... G06F 2203/04109; G06F 3/0325; G06F 3/041; G06F 3/042; G06F 3/0421;
(Continued)

(56) References Cited

U.S. PATENT DOCUMENTS 3,673,327 A * 6/1972 Johnson ................ G06F 3/0421
178/18.04
4,006,627 A * 2/1977 Bossaert ................ G01H 9/002
73/608
(Continued)

FOREIGN PATENT DOCUMENTS

CN 101592499 A 12/2009 ............... G01D 5/24
CN 102124362 A 7/2011 ............... G01S 5/14
(Continued)

OTHER PUBLICATIONS

Lai et al. "Pressure Indicating Film Characterization of Wafer-to-Wafer Bonding". Apr. 7, 2009. <http://www.sensorprod.com/news/white-papers/2009-04_wb/wp_wb-2009-04.pdf>.*
(Continued)

*Primary Examiner* — Jonathan Dunlap
(74) *Attorney, Agent, or Firm* — Kusner & Jaffe (57) ABSTRACT

A measuring device for determining a pressure map during application of pressure to at least one measurement layer between a first pressure body and a second pressure body the measuring device comprising: (i) at least one transmitter located on one peripheral edge of the measurement layer for emission of signals in the form of electromagnetic waves along a first signal route which runs through the measurement layer and at least one other signal route which runs through the measurement layer, and (ii) at least one receiver located on the peripheral edge for reception of the signals of the first signal route and other signal route(s), which signals are sent by the transmitter through the measurement layer and can be changed when pressure is applied. Furthermore this invention relates to a corresponding method.

21 Claims, 4 Drawing Sheets

(51) Int. Cl.
| | |
|---|---|
| *H01L 21/66* | (2006.01) |
| *G01L 5/00* | (2006.01) |
| *G01L 11/02* | (2006.01) |
| *G01N 21/17* | (2006.01) |
| *G06F 3/042* | (2006.01) |
| *G01L 9/00* | (2006.01) |
| *G01N 23/046* | (2018.01) |
| *G06F 3/041* | (2006.01) |
| *G06F 3/03* | (2006.01) |

(52) U.S. Cl.
CPC ........... *H01L 22/12* (2013.01); *G01L 1/24* (2013.01); *G01L 1/241* (2013.01); *G01L 9/0076* (2013.01); *G01L 11/02* (2013.01); *G01N 23/046* (2013.01); *G01N 2021/1787* (2013.01); *G01N 2223/419* (2013.01); *G06F 3/0325* (2013.01); *G06F 3/041* (2013.01); *G06F 3/042* (2013.01); *G06F 3/0421* (2013.01); *G06F 3/0423* (2013.01); *G06F 3/0428* (2013.01); *G06F 2203/04109* (2013.01)

(58) Field of Classification Search
CPC ... G06F 3/0423; G06F 3/0428; G01N 23/046; G01N 2223/419; G01N 2021/1787; G01L 9/0076; G01L 11/02; G01L 1/24; G01L 1/241; G01L 1/25
USPC ............. 250/227.14; 345/173, 175; 356/136, 356/300, 32, 432, 445, 485; 73/800, 818, 73/862.046, 862.624
See application file for complete search history.

(56) References Cited

U.S. PATENT DOCUMENTS

| | | | | |
|---|---|---|---|---|
| 4,328,707 A * | 5/1982 | Clement | ........... | A61B 8/14 600/442 |
| 4,536,651 A * | 8/1985 | Bosse | ........... | G01G 3/12 177/DIG. 6 |
| 4,562,540 A * | 12/1985 | Devaney | ........... | G01S 15/8977 128/916 |
| 4,799,382 A * | 1/1989 | Sprunt | ........... | G01N 15/088 378/4 |
| 4,899,046 A * | 2/1990 | Wright | ........... | G01F 1/3245 250/227.14 |
| 4,901,584 A * | 2/1990 | Brunner | ........... | G01L 1/247 250/227.14 |
| 5,063,509 A * | 11/1991 | Coles | ........... | G01N 23/046 250/269.1 |
| 5,524,636 A * | 6/1996 | Sarvazyan | ........... | A61B 1/0052 600/587 |
| 5,577,501 A * | 11/1996 | Flohr | ........... | G01N 23/046 378/4 |
| 5,764,161 A * | 6/1998 | Schier | ........... | G01B 11/16 340/870.16 |
| 5,970,111 A * | 10/1999 | Samarasekera | ........... | G01N 23/046 378/4 |
| 6,016,703 A * | 1/2000 | Blyler, Jr. | ........... | G01L 1/24 250/231.19 |
| 6,264,365 B1 * | 7/2001 | Patch | ........... | A61B 6/032 250/252.1 |
| 6,477,221 B1 * | 11/2002 | Ning | ........... | A61B 6/032 378/4 |
| 6,519,355 B2 * | 2/2003 | Nelson | ........... | G01N 15/147 382/133 |
| 6,522,775 B2 * | 2/2003 | Nelson | ........... | G01N 15/147 382/133 |
| 6,538,644 B1 * | 3/2003 | Muraoka | ........... | G06F 3/0421 345/156 |
| 6,568,273 B2 * | 5/2003 | Reimer | ........... | G01D 5/268 250/227.14 |
| 6,636,623 B2 * | 10/2003 | Nelson | ........... | G01N 15/1475 382/133 |
| 6,944,322 B2 * | 9/2005 | Johnson | ........... | G01N 15/14 382/128 |
| 7,372,937 B2 * | 5/2008 | Wang | ........... | G01N 23/046 378/16 |
| 7,418,075 B2 * | 8/2008 | Taguchi | ........... | A61B 6/032 378/15 |
| 7,463,179 B2 * | 12/2008 | Brady | ........... | G06T 9/00 341/155 |
| 7,738,945 B2 * | 6/2010 | Fauver | ........... | G01N 15/1468 356/444 |
| 7,777,891 B2 * | 8/2010 | Hasegawa | ........... | A61B 5/0059 356/485 |
| 8,009,276 B1 * | 8/2011 | Kirby | ........... | G01L 1/25 356/32 |
| 8,041,415 B2 * | 10/2011 | Shiina | ........... | A61B 5/0048 600/433 |
| 8,124,013 B1 * | 2/2012 | Gregoire | ........... | H05H 1/46 204/157.15 |
| 8,143,600 B2 * | 3/2012 | Seibel | ........... | G01N 21/4795 250/461.2 |
| 8,149,211 B2 * | 4/2012 | Hayakawa | ........... | G01L 1/205 178/18.05 |
| 8,345,254 B2 * | 1/2013 | Prystupa | ........... | G01N 21/552 356/432 |
| 8,364,414 B2 * | 1/2013 | Masumura | ........... | A61B 5/0073 356/432 |
| 8,368,035 B2 * | 2/2013 | Seibel | ........... | G01N 21/4795 250/461.2 |
| 8,382,670 B2 * | 2/2013 | Shiina | ........... | A61B 5/0048 600/437 |
| 8,447,087 B2 * | 5/2013 | Wong | ........... | A61B 1/00009 348/66 |
| 8,482,547 B2 * | 7/2013 | Christiansson | ........... | G06F 3/0421 178/18.09 |
| 8,542,217 B2 * | 9/2013 | Wassvik | ........... | G06F 3/0423 178/18.09 |
| 8,581,884 B2 * | 11/2013 | Fahraeus | ........... | G06F 3/0421 345/175 |
| 8,686,974 B2 * | 4/2014 | Christiansson | ........... | G06F 3/0421 178/18.09 |
| 8,692,807 B2 * | 4/2014 | Fohraeus | ........... | G06F 3/0418 178/18.09 |
| 8,780,066 B2 * | 7/2014 | Christiansson | ........... | G06F 3/0421 178/18.01 |
| 8,803,848 B2 * | 8/2014 | Suarez Rovere | ........... | G06F 3/0421 345/176 |
| 8,919,204 B2 * | 12/2014 | Fujino | ........... | G01L 1/241 73/800 |
| 9,041,408 B2 * | 5/2015 | Gregoire | ........... | G01N 3/00 250/227.11 |
| 9,092,091 B2 * | 7/2015 | Piot | ........... | G06F 3/042 |
| 9,250,794 B2 * | 2/2016 | Suarez Rovere | ........... | G06F 3/0488 |
| 9,274,645 B2 * | 3/2016 | Christiansson | ........... | G06F 3/0416 |
| 9,377,884 B2 * | 6/2016 | Christiansson | ........... | G06F 3/0421 |
| 9,411,444 B2 * | 8/2016 | Christiansson | ........... | G06F 3/0428 |
| 9,554,709 B2 * | 1/2017 | Fukutani | ........... | A61B 5/0095 |
| 9,557,846 B2 * | 1/2017 | Baharav | ........... | G06F 3/0421 |
| 9,671,900 B2 * | 6/2017 | Piot | ........... | G06F 3/042 |
| 2001/0011480 A1 * | 8/2001 | Reimer | ........... | G01D 5/268 73/705 |
| 2002/0075243 A1 * | 6/2002 | Newton | ........... | G06F 3/0421 345/173 |
| 2002/0141625 A1 * | 10/2002 | Nelson | ........... | G01N 15/147 382/131 |
| 2002/0150285 A1 * | 10/2002 | Nelson | ........... | G01N 15/147 382/131 |
| 2002/0154727 A1 * | 10/2002 | Ning | ........... | A61B 6/032 378/4 |
| 2003/0031352 A1 * | 2/2003 | Nelson | ........... | G01N 15/1475 382/131 |
| 2004/0075826 A1 | 4/2004 | Ro et al. | ........... | 356/73.1 |
| 2004/0076319 A1 * | 4/2004 | Fauver | ........... | G01N 15/1468 382/133 |

(56) References Cited

U.S. PATENT DOCUMENTS

| | | | |
|---|---|---|---|
| 2004/0252091 A1* | 12/2004 | Ma | G06F 3/0421 345/87 |
| 2006/0050842 A1* | 3/2006 | Wang | G01N 23/046 378/16 |
| 2006/0114237 A1* | 6/2006 | Crockett | G06F 3/0421 345/173 |
| 2007/0075648 A1* | 4/2007 | Blythe | G06F 3/0421 315/149 |
| 2007/0144273 A1* | 6/2007 | Decoster | B60R 21/01532 73/862.391 |
| 2007/0165774 A1* | 7/2007 | Taguchi | A61B 6/032 378/15 |
| 2008/0228033 A1* | 9/2008 | Tumlinson | A61B 1/00096 600/112 |
| 2009/0005685 A1* | 1/2009 | Nagae | A61B 5/0059 600/459 |
| 2009/0015834 A1* | 1/2009 | Csutak | G01D 5/268 356/365 |
| 2009/0073453 A1* | 3/2009 | Hasegawa | A61B 5/0059 356/477 |
| 2009/0135162 A1* | 5/2009 | Van De Wijdeven | G06F 3/0421 345/175 |
| 2009/0153519 A1* | 6/2009 | Suarez Rovere | G06F 3/0421 345/173 |
| 2009/0175407 A1* | 7/2009 | Harer | A61B 6/032 378/20 |
| 2009/0237656 A1* | 9/2009 | Ma | G01J 3/02 356/300 |
| 2010/0073674 A1* | 3/2010 | Yoshida | A61B 5/0073 356/300 |
| 2010/0094561 A1* | 4/2010 | Masumura | A61B 5/0073 702/19 |
| 2010/0204916 A1 | 8/2010 | Garin | 701/208 |
| 2011/0303015 A1* | 12/2011 | Ichihara | A61B 5/0091 73/656 |
| 2012/0013722 A1* | 1/2012 | Wong | A61B 1/00009 348/66 |
| 2012/0250001 A1* | 10/2012 | Tanaka | G01L 1/247 356/32 |
| 2012/0255365 A1* | 10/2012 | Wimplinger | H01L 21/67092 73/760 |
| 2013/0044073 A1* | 2/2013 | Christiansson | G06F 3/0421 345/173 |
| 2013/0107258 A1* | 5/2013 | Csutak | G01D 5/268 356/365 |
| 2013/0199310 A1* | 8/2013 | Fujino | G01L 1/241 73/862.624 |
| 2013/0201142 A1* | 8/2013 | Suarez Rovere | G06F 3/0421 345/173 |
| 2013/0249833 A1* | 9/2013 | Christiansson | G06F 3/0428 345/173 |
| 2013/0285968 A1* | 10/2013 | Christiansson | G06F 3/0416 345/173 |
| 2013/0307795 A1* | 11/2013 | Suarez Rovere | G06F 3/0488 345/173 |
| 2014/0098058 A1* | 4/2014 | Baharav | G06F 3/0421 345/174 |
| 2014/0102221 A1* | 4/2014 | Rebhan | B30B 15/062 73/862.381 |
| 2014/0125633 A1* | 5/2014 | Fahraeus | G06F 3/0421 345/175 |
| 2014/0152624 A1* | 6/2014 | Piot | G06F 3/042 345/175 |
| 2014/0197848 A1* | 7/2014 | Gregoire | G01N 3/00 324/637 |
| 2014/0292701 A1* | 10/2014 | Christiansson | G06F 3/0421 345/173 |
| 2014/0300572 A1* | 10/2014 | Ohlsson | G06F 3/042 345/173 |
| 2016/0018280 A1* | 1/2016 | Hendricks | G01L 11/02 73/705 |
| 2016/0034095 A1* | 2/2016 | Piot | G06F 3/042 345/175 |
| 2017/0269777 A1* | 9/2017 | Piot | G06F 3/042 |

FOREIGN PATENT DOCUMENTS

| | | | |
|---|---|---|---|
| GB | 2 141 821 A | 1/1985 | G01L 1/24 |
| JP | S57-27834 Y2 | 6/1982 | D04B 1/10 |
| JP | S58-132840 U | 9/1983 | G01L 5/00 |
| JP | H04-120432 A | 4/1992 | G01L 1/24 |
| JP | H10-19785 A | 1/1998 | G01N 21/27 |
| JP | 2000-003841 A | 1/2000 | H01L 21/02 |
| JP | 2002-219108 A | 8/2002 | A61B 5/00 |
| JP | 2014-138618 A | 5/2004 | G01M 11/00 |
| WO | WO 2012/167814 A1 | 12/2012 | G01L 5/00 |

OTHER PUBLICATIONS

International Preliminary Report on Patentability from corresponding International Patent Application No. PCT/EP2013/061583, dated Sep. 8, 2015 (English-language translation provided).

International Search Report from corresponding International Patent Application No. PCT/EP2013/061583, dated Jan. 31, 2014 (English-language translation provided).

* cited by examiner

MEASURING DEVICE AND METHOD FOR ASCERTAINING A PRESSURE MAP

FIELD OF THE INVENTION

This invention relates to a measuring device and a method.

BACKGROUND OF THE INVENTION

In the semiconductor industry, in general substrates of different sizes, shapes and materials are joined to one another. The joining method is called wafer bonding. Wafer bonding is roughly divided into permanent and temporary bonding. In permanent bonding a no longer detachable connection between the substrates is formed. This permanent connection takes place for example by interdiffusion of metals, by cation-anion transport in anodic bonding or by the formation of covalent bonds between oxides and/or semiconductor materials in fusion bonding, and in the crosslinking of polymers in bonds with organic cements.

In temporary bonding mainly so-called bonding adhesives are used. They are adhesives which are applied to the surface of one or both substrates by a coating method in order to act as adhesive between the substrates.

In all bonding methods bonders are used to apply a blanket pressure as uniform as possible to the substrates to be bonded to one another. Here it is of very great importance that the pressure distribution along the surface of the substrates is optimum. Otherwise voids can arise due to gas inclusions, by squeeze-out, by absent grain growth and by nonuniform layer thicknesses.

Pressure inhomogeneities can be attributed mainly to poorly manufactured pressure disks, wafer chucks or to their wear. Furthermore the different elastic properties of the components which generate the compressive load on the substrates are responsible for many pressure inhomogeneities. This is mainly the case when the moduli of elasticity of the components of the bonder are smaller than the moduli of elasticity of the substrates to be bonded or the layers which are located between the substrates. In order to obtain a corresponding elasticity of the bonder, pressure disks, wafer chucks or compensation disks produced from special materials such as graphite are used to obtain the optimum bonder configuration. In very many cases for example graphite compensation disks of corresponding size are fixed between the pressure disk and the piston. The use of these compensation disks depends on the respective configuration and the bond type. Graphite compensation disks have been used most often to date since they deform very well, are temperature-stable and have a corresponding modulus of elasticity under full compressive loading. Generally the use of these compensation disks improves the pressure homogeneity.

Therefore methods are known for obtaining quantitative information about the pressure distributions along the pressure surfaces.

The most frequently used method is the evaluation of the color information on paper which is colored to different degrees by bursting of color balls at high pressure. Although this method is current practice, it has disadvantages. Cutting out the films, installing them between the pressure bodies and removing them are accordingly time-consuming. Moreover the material cannot be used under thermal loading due to high temperature sensitivity; this also causes problems in the reproducibility of the results. Another problem is the numerical evaluation of the pressure data, which evaluation is not reliable or reproducible.

A second already known method was disclosed in WO2012/167814A1. This method is based on the evaluation of the deformation of fluid particles caused by the compressive load. This method does not allow in-situ measurement of the pressure distribution between the pressure bodies either.

A third, already known method uses a measuring device of hundreds of locally distributed pressure sensors which must be produced on a corresponding substrate, which method is complex and especially costly. Production takes place using microsystems technology. The microsensors are MEMS and/or semiconductor elements which can control a current, depending on the respective compressive loading.

SUMMARY OF THE INVENTION

The object of this invention is therefore to devise a measuring device and a method for determining a pressure map with which the aforementioned disadvantages are at least largely eliminated.

This object is achieved with the features of the independent claim(s). Advantageous developments of the invention are given in the dependent claims. All combinations of at least two of the features given in the specification, the claims and/or the figures also fall within the scope of the invention. At the given value ranges, values within the indicated limits will also be considered to be disclosed as boundary values and will be claimed in any combination.

The basic idea of this invention is to measure at least one physical parameter of at least one electromagnetic wave or several electromagnetic waves after passing through a measurement layer, especially in-situ, and to compute from the measured data a pressure, preferably a pressure distribution, in the measurement layer. Preferably all physical parameters of all waves, which parameters are to be measured, are measured before entering the measurement layer and afterwards. The measurement comprises a plurality of signal routes of the electromagnetic waves, therefore measured distances, and from the different, especially crossing signal routes in the measurement layer, localized pressure values can be determined from the measurement results and in this way a pressure map can be prepared, especially in-situ. This can be electronically displayed, especially in-situ, since there is a functional relationship and thus electronic processing is enabled. Preferably a measurement is taken before and/or during and/or after compressive loading. Accordingly a complete pressure map is determined before and/or during and/or after the compressive loading. The determination of the pressure maps before compressive loading is preferably used for calibration. The determination of the pressure map during compressive loading is used preferably to determine an in-situ state. The determination of the pressure map after compressive loading is used preferably for determining the post-state. Preferably the pressure maps can also be compared among one another.

The physically useful wavelength range of the electromagnetic waves used extends from the microwave range to the x-ray range. Preferably electromagnetic waves in the visible light range are used. The electromagnetic beams used have especially a wavelength between $10^{-12}$ m and 1 m, preferably between $10^{-9}$ m and $10^{-3}$ m, most preferably between $10^{-7}$ m and $10^{-5}$ m.

The invention is based on the further idea of using pressure-dependent optical properties of a measurement material of the measurement layer, hereinafter also called "optical material", for determining a pressure distribution.

In other words, the invention describes a measuring device and a corresponding method to determine the pressure distribution in a measurement layer which is exposed to tension or pressure by two pressure bodies, in-situ and/or locally resolved, especially absolutely and/or depending on the temperature. The invention is furthermore based on the idea of determining locally resolved the change of the optical properties of the measurement layer which is located between the pressure bodies during the change of the pressure application. The optical properties and their changes when exposed to pressure are correlated to the pressure or are transformed into a pressure map.

The invention is based on the further idea of measuring, locally resolved, the pressure dependency of one or more optical property (properties) of the measurement layer between the two pressure bodies with at least one transmitter and at least one detector/receiver or in particular to determine it, in particular compute it from a cumulative measurement signal by means of mathematical analysis such as especially Radon transform, relative to the location of the respective pressure value, so that a pressure map arises therefrom.

Methods of the invention are methods for reconstruction of the video signals of a volume, especially the Radon transform. This is the best known of all methods which is used for example for tomographic reconstruction in medical technology. The principle is the inversion of the integral which arises by summation of individual events along a path and which arises via the measurement along several directions of space.

In the low-coherence tomography approach it is also especially possible to combine the approach of the invention with a transit time analysis—here the local reconstruction is refined only along an ellipse (with the detector and transmitter at the focal point).

Cumulated measurement signals are attributed to locally discrete measurement signals by means of the aforementioned mathematical and physical models. It is therefore disclosed that any mathematical algorithm using which conversions can be carried out between the local compressive load and the output signals is suitable for pursuing the embodiments of the invention.

The correlation between the (local) optical properties and the prevailing (local) pressure conditions can be established theoretically and/or empirically. There are very exact physical models using which the relationship between material properties and/or optical and/or mechanical properties can be described. But empirical determination and mainly calibration are preferred in the invention. In a first embodiment the empirical calibration takes place mainly in that blanket pressure application to the measuring device takes place with a defined force, at a certain temperature. In the ideal case the determined change of the optical properties and thus the pressure application should be independent of the site and thus deliver a homogeneous pressure map. Based on the fact that not all components which cause the pressure to be applied can be perfectly produced, for a corresponding calibration process pressure maps or maps of the change of optical properties, hereinafter simply called maps, are determined which constitute a slight deviation from the ideal state. Dedicated remachining of the components used, therefore matching of the machine or the components, or a use of the just determined map as a "zero map", would be conceivable. The determined zero map is especially vector-subtracted from the map which has been determined later in the actual bond process.

In another special embodiment the measuring device is calibrated as follows. The measuring device is loaded in steps, especially at points, with a corresponding pressure body. The pressure body has an extremely thin tip. The force applied by the pressure body to the measuring device is monitored and/or set and/or measured via a dynamometer on the pressure body. At the same time, for each point load a signal is recorded which can be attributed unambiguously to the corresponding point loading. The preset point loading of the embodiment of the invention enables not only a calibration of the measuring device, but also setting the zero point so than any inhomogeneities which are present in the measuring device and which can disrupt the local pressure evaluation can be a priori precluded.

The invention thus comprises the following approaches/advantages:
  an in-situ measurement of the pressure distribution along the pressure surfaces of the substrates is enabled so that the pressure distribution can be evaluated before and/or preferably during the bond process, especially within the bond chamber,
  it becomes possible to determine the pressure distribution directly in a bond interface or in any layer of the substrate stack, especially within a temporary bond layer, for example a cement and/or during a bond process without placing a measuring device between the pressure bodies,
  localized, especially absolute pressure values of the pressure distribution, also over relatively large pressure surfaces, can be determined with high precision and over a large temperature range with high local resolution,
  essentially no material consumption.

The invention allows in-situ measurement of the pressure distribution between two pressure bodies. Sensors designed accordingly can be re-used, are flexible, can be installed quickly in any type of bonder, and viewed over the long term are more economical than the (very expensive) pressure films according to the prior art, less labor-intensive and thus allow prompt and targeted process optimization. Another advantage of the invention includes being able to determine the pressure distribution even under any temperature load. The optical properties of a material depend generally on the temperature. In this case the relationship between the change of the optical properties and the temperature can be known and can then be used to carry out corresponding expanded calibration of the measuring device for different temperatures. The expanded calibration then corresponds to several individual calibrations at different temperatures.

To determine the pressure distribution of two pressure bodies which is arising, the measuring device as a sensor is placed on the lower, second pressure body. The pressure bodies move into contact with the sensor. The pressure distribution which arises between the pressure bodies loads the optical material of the measurement layer and thus changes an optical property of the material of the measurement layer which is dependent on pressure. For locally dependent determination of the pressure distribution as the pressure map, an optical signal is injected on the edge of the measurement layer, therefore sent into the measurement layer by a least one transmitter. The signal penetrates the measurement layer along one measured distance or one surface segment and is captured and measured by at least one receiver made as a detector on one side which faces away from the transmitter, preferably exactly opposite. The signal sent in this way through the measurement layer has experienced at least one (cumulatively acquired) change of at least one of its optical properties along the signal route or several signal routes when pressure is applied.

A pressure map can be determined the invention by recording several especially crossing signal routes.

For example, the following, individually or in combination, are conceivable as properties which are to be acquired by the receiver:
 (change of) intensity,
 (change of) polarization,
 (change of) wavelength or frequency,
 (change of) index of refraction,
 (change of) mode Since the signals captured by the receiver or the receivers are the result of cumulation of all signal changes along the respective signal route, a mathematical transformation is used to obtain the change of the optical property of the optical material in the measurement layer as a function of site. For this reason several measurements are picked up with different transmitter and/or receiver positions along the peripheral edge of the measurement layer and/or the measuring device, in particular any signal route crossing with at least one other signal route.

The cumulated output signals are each recorded as a function of the angular position of the transmitter and/or detector. A mathematical transform for converting the cumulated signals into the change of the optical signals as a function of the position within the measurement layer for preparing a pressure map is for example the Radon transform. By using the Radon transform the change of the optical property is obtained at any site, especially at crossing points of signal routes which cross, of one of the acquired signal routes of the optical material as a function of pressure. Since the change of the optical property (properties) of the optical material can be correlated with the pressure, there is thus the possibility of recording the pressure distribution between the pressure bodies.

Furthermore embodiments of the invention are described with which the pressure distribution can be determined.

In a first embodiment of the invention the optical material is distributed in a blanket manner over the entire measurement layer. For all following embodiments of the invention, electromagnetic signals, which are injected by a transmitter at least one site on the peripheral edge of the measurement layer, run along one signal route or preferably superficially, therefore with several signal routes. Along the signal routes at least one of their physical properties changes based on the pressure distribution which is to be determined.

The detector (receiver) at the outlet of the signal from the measurement layer (therefore at the end of each signal route) therefore acquires a measurement signal which is either summed (cumulated) or changed at least continuously along the measured distance. Viewed mathematically, therefore the cumulated change on the recorded properties is imaged along each signal route by an imaging standard in a measurement signal or acquired as a value.

In order to determine the pressure distribution the transmitter and/or detector/receiver are moved along the outside contour or of the peripheral edge of the measurement layer and several measurement signals of several signal routes are determined and they are converted with a mathematical transform to the local measurement signals. The local measurement signals are then unambiguously dependent on the local compressive load. The preferred transform for conversion is the Radon transform. The mathematical relationships between the determined measured values of the physical and/or optical properties and the pressure are especially empirically determined.

In one preferred embodiment of the invention on one or on several pressure surfaces of the measurement layer there can be one reflection layer at a time in order to influence the optical properties of the measurement layer or the measured values as little as possible by the substrate or pressure body and to deliver a reproducible result.

In a first embodiment of the invention the measurement layer is part of a separate sensor as a measuring device. In each embodiment the sensor includes a lower substrate, a measurement layer and an upper substrate. The substrates preferably have the shape of the pressure sensor or in general a shape dictated by the measurement range. They can be made rectangular, round or of any other shape. Preferably the substrates have a round shape. For round substrates the diameter is greater than $10^{-3}$ m, preferably greater than $10^{-2}$ m, more preferably greater than $10^{-1}$ m, most preferably greater than 1 m. If the sensor is used for pressure distribution measurements in the semiconductor industry, the diameter of the substrates is preferably 1 inch, 2 inches, 3 inches, 4 inches, 5 inches, 6 inches, 8 inches, 12 inches, 18 inches, or more than 18 inches.

The thickness of the substrates depends on the application. In most cases the thickness is greater than 10 μm, preferably greater than 100 μm, more preferably greater than 1000 μm, most preferably greater than 2000 μm, most preferably of all greater than 5000 μm. Generally the thicknesses of the two substrates can be different. Preferably the thicknesses of the substrates of the sensor should correspond to the thicknesses of the substrates to be bonded later in reality. The absolute amount between the thicknesses of the substrates of the sensor and the substrates to be bonded later in reality should be smaller than 1 mm, preferably smaller than 0.1 mm, more preferably smaller than 0.01 mm, most preferably smaller than 1 μm, most preferably smaller than 0.1 μm, most preferably of all smaller than 0.01 μm.

In order to ensure optimum, complete and mainly homogenous pressure transfer between the pressure bodies and the measurement layer, each substrate has a thickness as uniform as possible. The total thickness variation (TTV) of a substrate is smaller than 100 μm, preferably smaller than 10 μm, more preferably smaller than 1 μm, most preferably smaller than 100 nm, most preferably of all smaller than 10 nm. The average roughness is smaller than 1000 nm, preferably smaller than 100 nm, more preferably smaller than 10 nm, most preferably smaller than 1 nm, most preferably of all smaller than 0.1 nm. Preferably the components, mainly the substrates used, of the sensor should have elastic properties which are as similar as possible to the substrates to be bonded later in reality. The absolute amount of the difference between the moduli of elasticity of the substrates of the sensor and the substrates to be bonded later in reality should be less than 1000 MPa, preferably less than 100 MPa, more preferably less than 10 MPa, most preferably less than 1 MPa.

The substrates are preferably mechanically isotropic in order to be able to transfer the pressure distribution from the pressure bodies homogeneously to the measurement layer. Therefore the substrates preferably have an amorphous microstructure.

When the microstructure of the substrates is polycrystalline, the substrates are preferably produced from a material whose crystallites have crystal-isotropic mechanical properties. This is the case mainly in materials with cubic crystal structure. Cubic materials therefore have preferably a Zener anisotropy factor (ZA) which is smaller than 9, preferably smaller than 7, more preferably smaller than 5, still more preferably smaller than 3, most preferably smaller than 2, most preferably of all 1. The solely known metal with a ZA of roughly 1 is tungsten. Tungsten is therefore disclosed as the metal preferred for a uniform pressure transfer.

One likewise preferred material for an embodiment of the invention is carbon, especially in the form of graphite, more preferably as a diamond.

In the case of a single-crystalline substrate it is preferably cut such that within one cutting plane it is mechanically isotropic (in-plane isotropic). In the case of a single-crystalline substrate which has a cubic crystal lattice, the substrate is therefore preferably cut such that its surface is a crystallographic (111) plane and the crystallographic direction <111> is normal to the substrate surface. In the case of a single-crystalline substrate which has a hexagonal crystal lattice, the substrate is preferably cut such that its surface is parallel to the crystallographic (0001) plane.

The optical material is distributed over the entire surface between the lower and upper substrate. The optical material can be applied by all known processes to the lower and/or upper substrate, preferably by PVD, CVD, PECVD, atomic layer deposition (ALD), molecule layer deposition (MLD), electrochemical deposition, plating, lamination, spin coating, spray enameling. Moreover the optical layer can also be produced from a homogeneous material block for example by lapping, polishing and grinding.

The lower substrate, the measurement layer and the upper substrate preferably form a preferably permanently connected sensor which cannot be separated. The type and manner in which lower substrate, measurement layer and upper substrate hold together is optional. The use of an optical material which at the same time acts as cement and which by a bond process can permanently cement the lower to the upper substrate is conceivable. Another possibility would be the welding of the measurement layer to the lower and upper substrate via the formation of a metal bond or fusion bond.

In a further embodiment of the blanket version, the measurement layer is not part of a specially produced sensor, but part of the wafer stack to be bonded.

The parts which are relevant are the transmitter, the measurement layer and the detector/receiver. The use of the optical properties of a layer of the wafer stack to be bonded allows one-time and completely novel measurement of the pressure distribution during the actual bonding process. The measurement principle can thus be applied to the layer as a measurement layer which is part of a substrate stack which is actually to be bonded. Therefore the measurement layer need not necessarily be the measurement layer of a separate sensor. With the disclosed method presented here the pressure distribution in one layer can also be measured in-situ in a bonder. The measurement layer must have at least one pressure-dependent optical property which is necessary.

The measurement signals of a blanket measurement layer with optical material are evaluated as follows:

In a first embodiment of the invention, the optical property of double refraction is used to obtain the pressure distribution in the measurement layer. Double refraction is defined as the process of splitting an incident ray into an ordinary and an extraordinary ray whose electrical or magnetic fields are polarized linearly to one another. Basically only optically anisotropic materials show double refraction. Generally optically isotropic materials under compressive load also become optically anisotropic. The optical material need therefore have at least optical anisotropy which is dependent on the pressure in order to cause the desired effect of double refraction.

One embodiment of the method of the invention includes injecting an electromagnetic, monochromatic signal of a transmitter via a polarizer into the measurement layer. The polarizer provides for only electromagnetic waves of a certain oscillation plane travelling into the measurement layer. The injected beam is generally divided into an ordinary and an extraordinary ray due to the optical property of double refraction. The oscillation planes of the electrical fields of the ordinary and extraordinary ray are turned by a local compressive load so that a receiver which is attached to the output of the measurement layer can detect the new oscillation planes of the ordinary and/or extraordinary beam. Preferably one of the two beams is completely absorbed on the path through the measurement layer along the signal route or preferably leaves the measurement layer. The ray which remains in the measurement layer preferably uses the physical phenomenon of total reflection in order to be worked through along the signal route as far as the end of the measurement layer. The signal incoming on the detector is therefore a rotation of the oscillation plane, which rotation has been changed along the signal route, especially at least predominantly, preferably exclusively by the pressure distribution along the measured distance. The local change of the oscillation plane is determined again by the recording of several measured distances by the motion of the transmitter and/or detector and the use of a corresponding mathematical transform, preferably the Radon transform.

In another embodiment of the invention, the optical property of the index of refraction is used to determine the pressure distribution in the measurement layer. The index of refraction of the optical material of the measurement layer in the unloaded state is greater than 1, preferably greater than 1.5, more preferably greater than 2.0, most preferably greater than 2.5, still most preferably greater than 3.0, most preferably of all greater than 3.5. The index of refraction of the materials which border the measurement layer, furthermore called boundary materials or substrate materials, in the unloaded state is especially greater than the index of refraction of the measurement layer, preferably smaller than 3.5, more preferably smaller than 3.0, most preferably smaller than 2.5, most preferably smaller than 2.0, still most preferably smaller than 1.5. Preferably the index of refraction of the boundary materials under compressive loading does not change or does change only very little. The injected signal is held by total reflection preferably largely in the measurement layer by the different indices of refraction between the optical material of the measurement layer and the boundary materials.

One idea of the invention is that the optical material is compressed by a local pressure change and thus a local change of the index of refraction of the optical material is caused. Thus the overflow behavior of the electromagnetic radiation from the measurement layer into the vicinity, therefore into the boundary materials or the substrates, changes. This is defined mainly as a local change of the intensity. The overflow behavior of the electromagnetic radiation is preferably described with the Fresnel equations. The signal incoming on the detector is therefore an intensity of the electromagnetic radiation which has changed along the signal route, especially predominantly, preferably exclusively, by the pressure distribution along the signal route. The determination of the local intensity and thus of the local index of refraction and of the local pressure takes place by recording several measured distances by the movement of the transmitter and/or detector along the peripheral edge and the use of the Radon transform.

In a third embodiment of the invention, transverse electromagnetic waves (TEM wave) are used as the optical property. A TEM wave is defined as an electromagnetic wave whose electrical and magnetic field components disappear in the propagation direction. TEM waves form only under boundary conditions. A boundary condition is defined as a limiting geometrical condition which dictates which function values the examined function, in the special case the electrical and/or magnetic field, has. Especially standing transverse electromagnetic waves are formed by the boundary conditions. The distribution of the electromagnetic field density in space is preferably strictly symmetrical. The different forms of the standing waves are called modes. The modes of the TEM waves are comparable to the standing waves of acoustics or the standing waves which can form in clamped cables.

Another idea of the invention is to inject a monochromatic electromagnetic wave into the measurement layer at a certain angle of incidence. One of the possible modes forms by the geometrical boundary conditions. In the measurement layer therefore standing transverse electromagnetic waves arise. If the intensity along the cross sectional surface is analyzed in a cross section of the measurement layer, a symmetrical intensity distribution is obtained. The symmetrical intensity distribution can be represented by a mathematical function for simple geometrical boundary conditions such as those of the extended thin measurement layer. This mathematical function contains so-called order parameters using which conclusions about the number of peaks are obtained.

The inventive idea of this embodiment of the invention therefore includes recording the intensity distribution on the receiver side. The geometry is changed by a compressive load along the measured distance such that the measurement layer becomes in particular thinner. This changes the boundary conditions for the TEM wave. The local change of the boundary conditions thus has an influence on the measured intensity signal at the end of the measured distance. In order to obtain the pressure distribution along the entire measurement surface, signals from several different detector positions are recorded at different transmitter positions. In the specific case the signals are not integrals, but surface signals. Therefore the intensity distribution along one solid angle around the normal of a surface detector is recorded. The local intensity distribution determined in this way in the measurement layer can again be linked to the pressure and thus allows the determination of the entire pressure distribution.

The number of transmitters is greater than or equal to one, preferably greater than 3, more preferably greater than 5, most preferably greater than 8. The number of detectors is greater than or equal to one, preferably greater than 3, more preferably greater than 5, most preferably greater than 8. In particular the transmitter and the receiver/detector are made integral or the transmitter and/or receiver are arranged especially uniformly and/or symmetrically on the peripheral edge of the measurement layer to be measured or are moved in rotation at a constant radius around the measurement layer. The transmitters can be made as point detectors, line detectors or preferably surface detectors. This measurement process can also be called tomography.

In another embodiment of the invention there are reflectors within the measurement layer. The reflectors are objects, preferably balls or cylinders, whose axis is parallel to the normal of the measurement layer or parallel to the pressure application direction and they have high reflectivity at the wavelength of the injected measurement signal. The transmitter injects electromagnetic radiation with a given frequency into the measurement layer. After a given time the detector measures an echo of the injected signal. The transmitter and detector can be located at different positions of the periphery of the measurement layer. The transmitter and detector are preferably synchronized so that the detector begins to measure time as soon as the transmitter injects the signal into the measurement layer. After a certain time the detector measures the echo signal of a reflector. The electromagnetic signal experiences a change in its intensity when it traverses a measurement layer. The intensity loss is a measure for the absorption along the signal route.

The pressure information at the position of a reflector arises by measuring the change of the output signal from the input signal. The decrease in intensity is preferably used as the measured quantity.

In another embodiment of the measuring device of the invention, as a separate sensor the optical material is part of one or more optical fibers which is/are distributed over the entire measurement layer or penetrate it from one entry site on the peripheral edge to an exit site on the peripheral edge. The fibers are embedded preferably in a mechanically anisotropic material, hereinafter call a matrix. In special embodiments the fibers are surrounded by a fluid, especially a liquid, in a quite special embodiment by a gaseous atmosphere.

In this connection an atmosphere is also defined as a vacuum.

The sensor includes a lower substrate, a measurement layer made as a matrix, at least one optical fiber embedded in the measurement layer, and an upper substrate. The corresponding transmitters and receivers as well as other optical devices are attached on the outside of the optical fibers and are used. The use of a silicone matrix in which the fibers are embedded would be conceivable. The sensor would then not have a corresponding upper and/or lower substrate, but would be made as a mat.

In one embodiment of the optical fiber version of the invention the optical fiber is rolled into a spiral, preferably an Archimedean spiral, and embedded in the matrix. At defined positions there are reference points at which the compressive stress is determined. The influence on the optical properties is not recorded at the end of the optical fiber, but at the input of the optical fiber. The distance of the reference point from the input is determined by a transit time measurement or special coding of the reference points.

In one preferred embodiment, in the direction of the normal of the measurement layer there is a pressure body which touches the optical fiber. The pressure body preferably has a high modulus of elasticity so that under a compressive stress, as much as possible it does not change its shape. The modulus of elasticity is greater than 10 MPa, preferably greater than 100 MPa, more preferably greater than 1 GPa, most preferably greater than 10 GPa, most preferably of all greater than 100 GPa, most ideally greater than 1000 GPa. By compressive stress on the optical fiber it is pressed onto the extremely stiff and thus poorly compressible pressure body so that its optical property changes locally. The change of the optical property changes can in turn be a change of the double refraction, a change in the index of refraction, and a change of the density of the optical material in the optical fiber. The transmitter is preferably a polychromatic source, more preferably a polychromatic, wavelength-selecting source, therefore a source using which one or more defined wavelengths or wavelength ranges can be selected and can be injected into the optical fiber. The position of each reference point at which a pressure body is located is accomplished by an interferometric measurement and/or a transit time measurement. In particular, the injection of a monochromatic wave is conceivable. The entry of the monochromatic wave into the optical fiber yields the time zero point. The monochromatic wave passes through the optical fiber. If the monochromatic wave is incident on a first pressure body, part of the wave is reflected. The reflected signal of the monochromatic wave is measured at the input by a detector. Thus the signal function and transit time for the first pressure body is known. The use of an interferometer for transit time difference measurement would also be conceivable. Part of the monochromatic wave travels beyond the first pressure body and is incident on the second pressure body which in turn results in a corresponding partial reflection. Accordingly analogous considerations apply to all further pressure bodies along the optical fiber. In one special embodiment it is conceivable to inject a polychromatic wave into the optical fiber, whose spectrum is preferably known at least in part. Corresponding interferometers enable a conclusion about the position of the pressure body and its signal shape. The use of different, wavelength-sensitive pressure bodies which preferably reflect only a certain part of the electromagnetic injected signal and thus can be broken down accordingly easily would also be conceivable.

In a second embodiment of the optical fiber version of the invention, there are several optical fibers. The optical fibers are located beyond the measurement layer in a grating. The grating is preferably set up rectangularly so that several optical fibers intersect one another at a right angle. Each of the optical fibers acts at the reference point as a pressure body for the optical fiber which is crossing it. At the input and the output of each optical fiber there are one transmitter (input) and one detector (output) respectively. The signal change under compressive stress is measured at the intersection points/reference points. At the intersection points two fibers lie together at one point transversely to one another and at the same time on top of one another. The compressive stress at this point compresses the optical material in the fibers; this leads to a change of double refraction, a change in the index of refraction, and a change in the density of the optical material in the optical fiber, and a change of the mode of the TEM wave. The evaluation of all measurement signals allows the determination of the origin of the change of the respective optical property and thus the conversion into the respective local pressure value.

The pressure distribution between the pressure bodies is measured at a die pressure of more than 1N, preferably more than 10 kN, more preferably more than 50 kN, still more preferably more than 100 kN.

The accuracy of the pressure values of the pressure measurement between the pressure bodies is better than 20%, preferably better than 15%, more preferably better than 10%, most preferably better than 5%, most preferably of all better than 1%.

The measurement can be taken at elevated temperatures. The measurement is taken at more than 0° C., preferably at more than 200° C., more preferably at more than 400° C., still more preferably at more than 600° C., most preferably of all at more than 800° C. The temperature has a reproducibility of better than 10%, preferably better than 5%, more preferably better than 1%, most preferably better than 0.5%, most preferably of all better than 0.1%.

To the extent the measuring device in a wafer processing device can be used especially in-situ, reproducible pressure distributions which can be displayed graphically can be determined. Moreover it is possible to deform the pressure surfaces of the pressure bodies accordingly based on the pressure map in order to optimize the pressure distribution of the pressure application. A further application would be the preparation and mainly the optimization of compensation disks using the determined pressure maps. Especially preferably the pressure maps are determined for optimization of the compensation disks again under conditions as real as possible, therefore with a substrate stack which is to be bonded accordingly in reality. Mainly bonders, grinders, polishing devices and metrology devices are considered a wafer processing device.

In one advantageous embodiment of the invention the transmitter/transmitters and/or the receiver/receivers can be moved along the peripheral edge. Advantageously the movement takes place controlled by the control apparatus, especially by means of stepping motors controlled by the control apparatus. Preferably the movement takes place along a path which is congruent in shape to the peripheral edge, especially a ring-shaped path, preferably an especially peripherally closed circular ring-shaped path.

Advantageously it is provided that the measuring device has several transmitters distributed on the peripheral edge and/or several receivers which are distributed on the peripheral edge and which are assigned to one, especially opposite transmitter at a time, especially at least two receivers per transmitter.

By the measure that each transmitter emits several signal routes especially at the same time and/or each receiver is assigned to one single signal route at a time, on the peripheral edge several receivers can be arranged as transmitters so that detection can take place more efficiently.

It is furthermore advantageous if the measuring device has one evaluation unit for determining localized pressure values of the pressure map along the signal routes, especially by a transform, preferably a Radon transform, which has signals received by at least one receiver.

According to other advantageous versions of the invention, at least one receiver can acquire signals which provide information about the optical behavior. The change of the signals is linked to a change of the optical properties and thus to a pressure change. In particular the following optical properties are important:
  double refraction
  index of refraction
  mode of signals shaped as transverse electromagnetic waves
  transit time
  spectral coding.

A method for determining a pressure map for pressure application to a measurement layer between a first pressure body and a second pressure body in its most general form comprises the following steps, especially the following sequence:
  arrangement of a measuring device as described above between the first pressure body and the second pressure body,
  emission of signals in the form of electromagnetic waves by the transmitter or transmitters located on the peripheral edge along a first signal route which runs through the measurement layer and at least one other signal route which runs through the measurement layer,
  reception of the signals by the receiver or receivers located on the peripheral edge for receiving the signals of the first signal route and other signal route(s), which signals are sent by the transmitter(s) through the measurement layer and which can be changed when pressure is applied.

For a device and the method of the invention the aforementioned features described for the measuring device apply accordingly and vice versa.

Other advantages, features and details of the invention will become apparent from the following description of preferred exemplary embodiments and using the drawings.

BRIEF DESCRIPTION OF DRAWINGS OF THE INVENTION

In the figures the same components or components with the same action are identified with the same reference numbers.

DETAILED DESCRIPTION OF THE INVENTION

Figure 1:
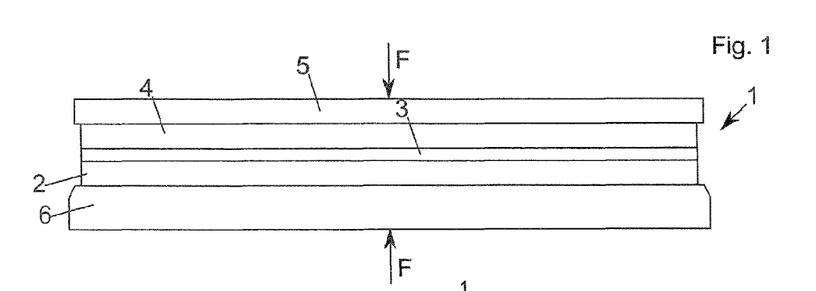
FIG. 1 shows a cross sectional view of a measurement arrangement with a measuring device.

FIG. 1 schematically shows a bond device, only a first upper pressure body 5 and a second lower pressure body 6 being shown in bonding with a bond force F which is directed transversely to the pressure surfaces of the pressure bodies 5, 6.

Between the pressure bodies 5, 6 there are a first substrate 2 and a second substrate 4 which are connected to a connecting layer made as a measurement layer 3 by application of a force with the bond force F.

The bond force F during application of pressure rises from zero shortly before making contact up to a bond force of up to several kN, from which a pressure referenced to the pressure surface arises, and the pressure surface can be computed for example for a round substrate with a diameter of 300 mm.

The measurement layer 3 is part of a measuring device for measuring optical properties of signals sent through the measurement layer 3, and the measuring device 1 can be either a sensor placed separately in the bond chamber as a measuring device or a measuring device 1 installed permanently in the bond chamber.

For measuring and transmitting electromagnetic waves, according to a first embodiment in FIG. 1 there is a transmitter 7 on one peripheral edge 3u of the measurement layer 3 which sends a signal 9 through the measurement layer 3 along one signal route.

For detection of the entire measurement layer 3, the transmitter 7 and/or the detector 8 can be moved, especially synchronized, along the peripheral edge 3u, especially along a ring-shaped, preferably round ring-shaped orbit which is shown by arrows. The orbit especially adjoins the measurement layer 3 indirectly.

There is a control apparatus (not shown) for controlling the components and method steps of the invention.

It is conceivable to distribute several transmitters 7 and/or several receivers 8 on the peripheral edge 3u which then cover one section of the peripheral edge 3u at a time, either by moving or by covering a larger component section.

Figure 2:
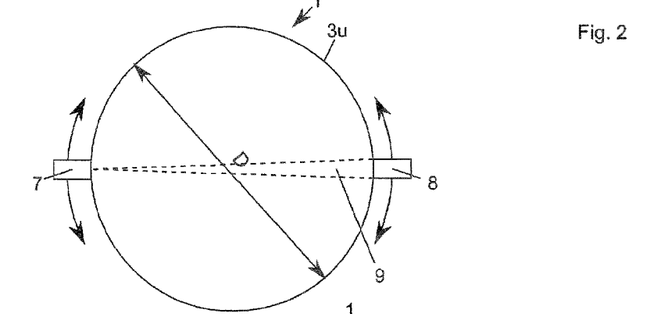
FIG. 2 shows a schematic plan view of a first embodiment of a measuring device.
Figure 3:
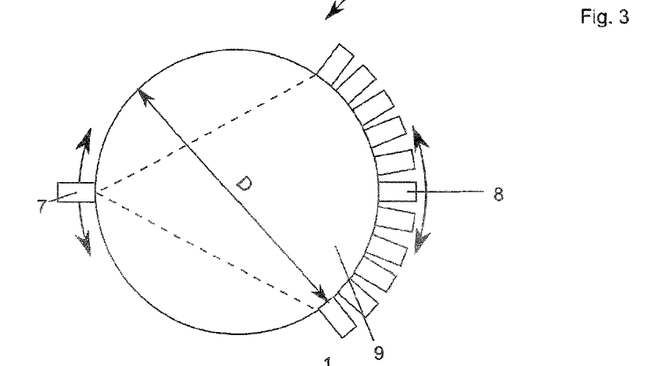
FIG. 3 shows a schematic plan view of a second embodiment of a measuring device.

Thus, in the second embodiment shown in FIG. 3 several receivers 8 are assigned oppositely to a single transmitter 7. The transmitter 7 compared to the first embodiment as shown in FIG. 2 emits a signal beam which acquires a larger section of the measurement layer 3 and has a plurality of signal routes which each lead to one of the receivers 8 and are recorded by it. Thus an advantage of this embodiment is that several signals can be detected at the same time along a larger angular section of the measurement layer 3. The required measurement time drops by the factor of the number of receivers 8.

By moving the transmitter 7 and the receiver 8 assigned to the transmitter 7 along the peripheral edge 3, the entire measurement layer 3 can be acquired. Alternatively there can be several transmitters 7 distributed on the periphery and respectively assigned receivers 8 so that the entire measurement layer 3 can be acquired without moving the transmitter and the receivers 8.

Figure 4:
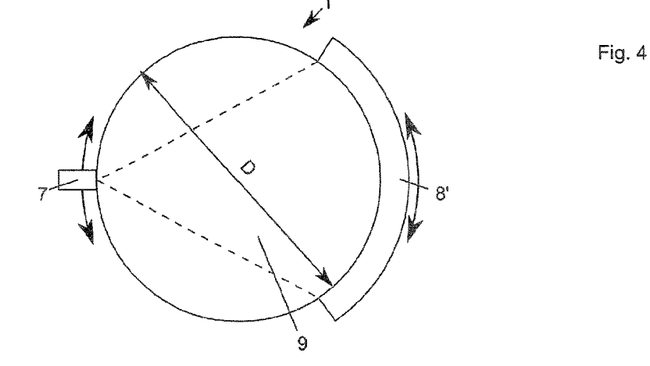
FIG. 4 shows a schematic plan view of a third embodiment of a measuring device.

FIG. 4 shows a third embodiment for acquisition of the measurement layer 3, there being a transmitter 7 and a receiver 8', the receiver 8' being equipped as a line detector or surface detector, especially as a CCD detector. The line detector or surface detector is able to record signals along one line or surface and to further process them directly. Depending on the local resolution of the receiver 8' it is made to acquire a plurality of signal routes of the signal 9. Analogously to the version as shown in FIG. 3 both the transmitter 7 and also the receiver 8' can be moved along the peripheral edge 3u or a plurality, especially three, transmitters 7 are distributed on the periphery, with receivers 8' respectively opposite.

It is common to the above described embodiments that essentially any plurality of signal routes running through the measurement layer 3 can be acquired by correspondingly small movement steps of the transmitters 7 and the receivers 8, 8'. The movement can take place especially by stepping motors which are controlled by the control apparatus.

Figure 5:
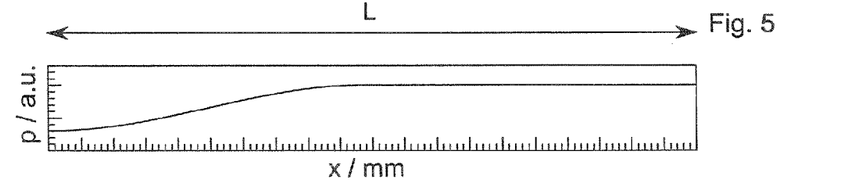
FIG. 5 shows a diagram of a local pressure distribution along a signal route L.

The acquired data are evaluated by an evaluation unit (not shown) which is shown in FIG. 5 in a diagram for an extract L of diameter D. In the diagram the local pressure distribution p evaluated by the evaluation unit is plotted against a route X and it can be recognized that the pressure p changes as a function of location. The diagram as shown in FIG. 5 is used as a reference for the pressure distribution in the embodiments which are shown by FIGS. 6 to 8 and which likewise relate to the extract L.

Figure 6:
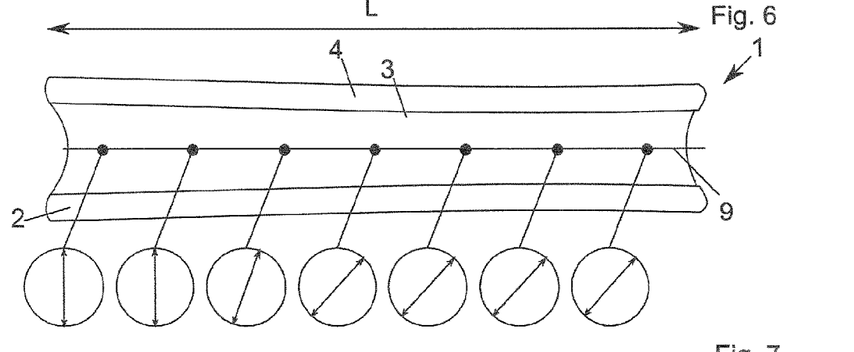
FIG. 6 shows a schematic of a measurement of an optical property of one embodiment of the measurement layer.

FIG. 6 shows how the double-refracting property of the optical material of the measurement layer 3 changes the polarization angle of the electrical field as a function of pressure. The polarization states are recorded on at least one of the receivers 8 on the end of the respective signal route after the signal 9 passes through the measurement layer 3.

Then the local polarization state is closed by a mathematical transform and from this the pressure is computed. This takes place in the evaluation unit. The propagation of the signal in this case is shown as a straight line since the physical parameter of the polarization is shown by corresponding arrows underneath FIG. 6. They correspond to the polarization states of the electrical field of the signal in the respectively shown point. The transformation and determination of the local position state are only possible by recording along different signal routes which cross one another.

Figure 7:
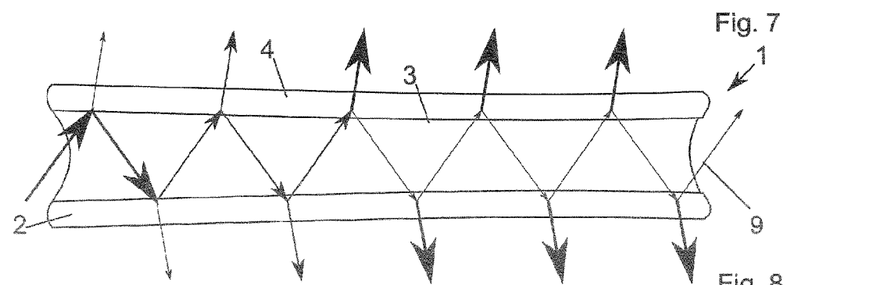
FIG. 7 shows a schematic of a measurement of an optical property of one embodiment of the measurement layer.
Figure 8:
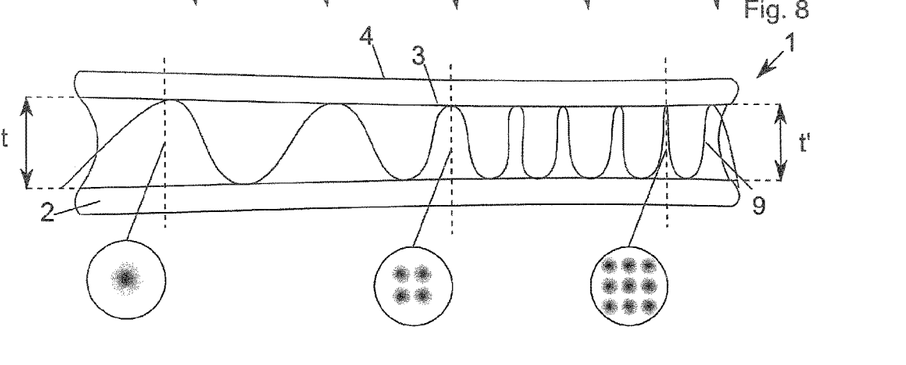
FIG. 8 shows a schematic of a measurement of an optical property of one embodiment of the measurement layer.

FIG. 7 shows the determination of another optical property of the optical material of the measurement layer 3, specifically the index of refraction. It can be recognized in the diagram according to FIG. 5 that the pressure rises from left to right within the distance L as a function of site. With rising pressure the optical material of the measurement layer 3 becomes denser and with rising density the index of refraction of the optical material also rises. By changing the index of refraction the reflection property of the signal 9 and thus its intensity change. The propagation of the signal 9 is represented by the direction of propagation of the electromagnetic wave of the signal 9 according to the rules of geometrical optics. The different thickness of the arrows schematically represents the intensity which is high at the entry of the signal 9 into the measurement layer 3. By changing the index of refraction with an advancing path, photons of the electromagnetic wave arise more and more by changing the refraction properties from the measurement layer 3; this is shown by arrows which become thinner and thinner. The arrows of the photons leaving the measurement layer 3 become thicker with increasing pressure. This optical property is also detected by acquiring several, especially crossing signal routes along the measurement layer 3 by a mathematical transform, especially a Radon transform.

FIG. 8 is a schematic of the change of a TEM wave by a pressure change which is caused by a pressure homogeneity along the path L. The compression changes the thickness of the measurement layer 3 along the path L from t to t', as a result of which the standing electromagnetic wave also changes within the measurement layer 3. This change of the electromagnetic wave leads to a change of the mode of the electromagnetic wave and also of the intensity distribution. A site-referenced determination of the pressure is possible from the change of the mode and/or intensity distribution, according to the invention a plurality of signal routes being evaluated. By measuring the intensity distribution of the modes along the peripheral edge $3u$ the intensity distribution of the mode at a certain location of the measurement layer 3 can be deduced by means of the transform, preferably a Radon transform. The local pressure can be determined from it.

Figure 9:
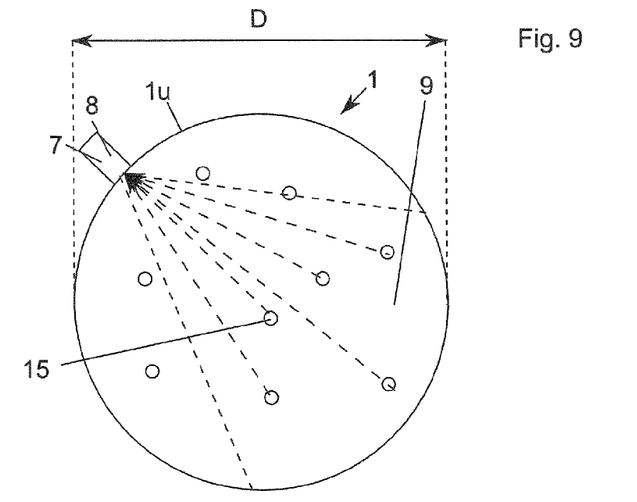
FIG. 9 shows a schematic plan view of a fourth embodiment of the measuring device.

FIG. 9 shows another embodiment of the invention with a transmitter-receiver unit including a transmitter 7 and a receiver 8. The transmitter-receiver unit sends and receives at the same location of the peripheral edge $3u$ of the measurement layer 3. The transmitter 7 of the transmitter-receiver unit injects an electromagnetic wave, specifically a divergent signal 9, into the measurement layer 3. The measurement signal 9 has a divergence with which a surface section of the measurement layer 3 is covered. The signal 9 of the electromagnetic wave is reflected on reflectors 15 to the receiver 8 of the transmitter-receiver unit. Pulsed operation and transit time measurement make it possible to draw conclusions about the signal path traversed by the recorded signal. A change of one of the above disclosed optical properties of the measurement layer, for example the intensity, polarization angle, mode of the TEM wave, is measured. The above described reflection method can obviate the necessity of exact alignment of the transmitter 7 to the receiver(s) 8 since they are mechanically connected and the position of the reflectors 15 is known.

Figure 10:
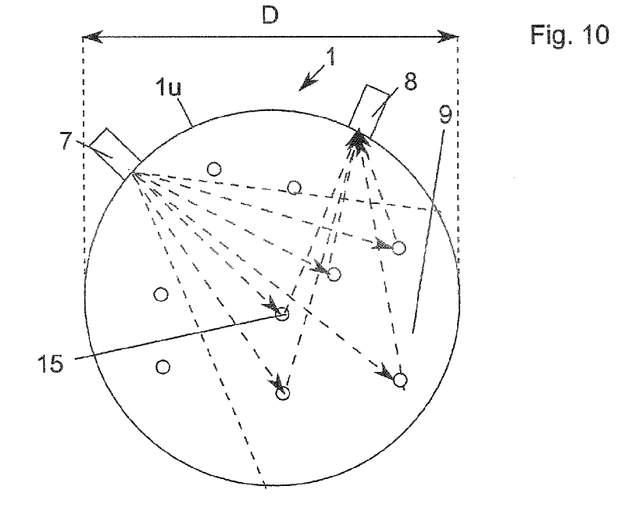
FIG. 10 shows a schematic plan view of a fifth embodiment of the measuring device.

In another embodiment as shown in FIG. 10, the transmitter 7 is separated locally from the receiver 8, but is electronically coupled to it so that calibration of the transmitter 7 to the receiver 8 can be done. Otherwise the embodiment of FIG. 10 corresponds to the above described embodiment of one reflection method according to FIG. 9.

Figure 11:
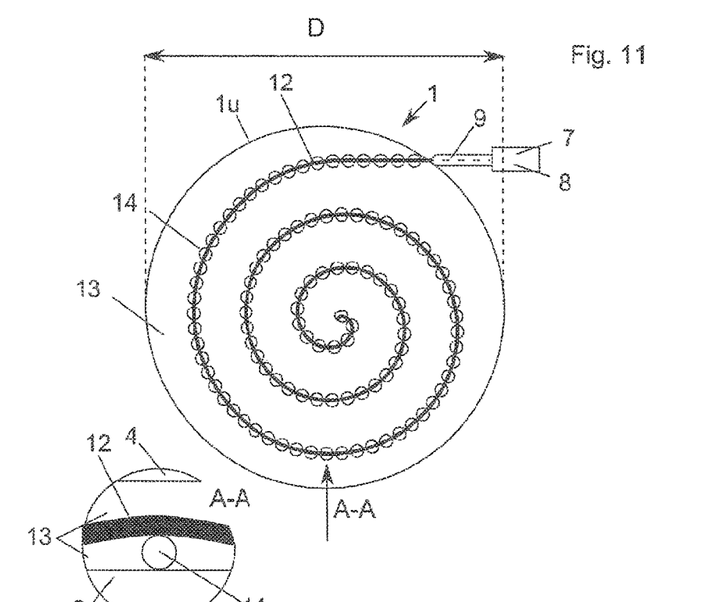
FIG. 11 shows a schematic plan view of a sixth embodiment of a measuring device.

In the embodiment shown in FIG. 11, the optical material of the measurement layer 3 is equipped with an optical fiber 12 which is distributed in the measurement layer 3. The fibers are preferably embedded into a mechanically isotropic material, a matrix. The illustrated embodiment is thus made as a separate measuring device in the form of a sensor, it is preferably comprised of a first substrate 2 and a second substrate 4 as well as the matrix which lies in between with optical fiber 12 and the measurement layer. Transmitters 7 and detectors 8 are each attached to the ends of the optical fiber 12 and otherwise are used as described above, the transmitter 7 and the receiver 8 being housed in a transmitter-receiver unit. It is accordingly also a reflection method. The transmitter-receiver units are each attached to the end of the optical fiber.

The use of a silicone matrix in which the optical fibers 12 are embedded is also conceivable. In this case the substrates 2, 4 can be omitted and the sensor can be made as a mat without an upper and a lower substrate.

The optical fiber 12 as shown in FIG. 11 is rolled as a spiral, preferably an Archimedean spiral, and is embedded in a matrix 13. At defined positions of the optical fiber 12 there are reference points at which the compressive stress can be determined. The reference points can be formed by especially spherical pressure elements 14. On the latter, depending on the pressure, an influence on the optical property of the optical fiber 12 occurs which can be assigned by means of a transit time measurement and/or spectral coding of the reference point. On the market there are corresponding transmitters and/or receiver units which emit a signal and which can again detect its reflection as a function of time and/or wavelength; they are known as such to one skilled in the art.

The optical property of the optical fiber 12 is locally changed at the reference points by the compressive stress of the optical fiber 12. The change of the optical property can be recorded, in particular a change of double refraction, a change in the index of refraction, and a change of the density of the optical material. They are recorded and evaluated by the transmitter-receiver unit.

The transmitter 7 in this case is preferably a polychromatic source, most preferably a polychromatic, wavelength-selecting source with which a defined wavelength can be detected and can be injected into the optical fiber 12. The position of each reference point at which a pressure element 14 is located is determined by interferometric measurement or a transit time measurement.

The pressure elements 14 preferably have a high modulus of elasticity so that this negative pressure stress does not experience any change of shape or does experience only the smallest possible change in shape. The modulus of elasticity can be in particular greater than 10 MPa, preferably greater than 100 MPa, more preferably greater than 1 GPa, most preferably greater than 10 GPa, most preferably of all greater than 100 GPa, even more preferably greater than 1000 GPa.

Figure 12:
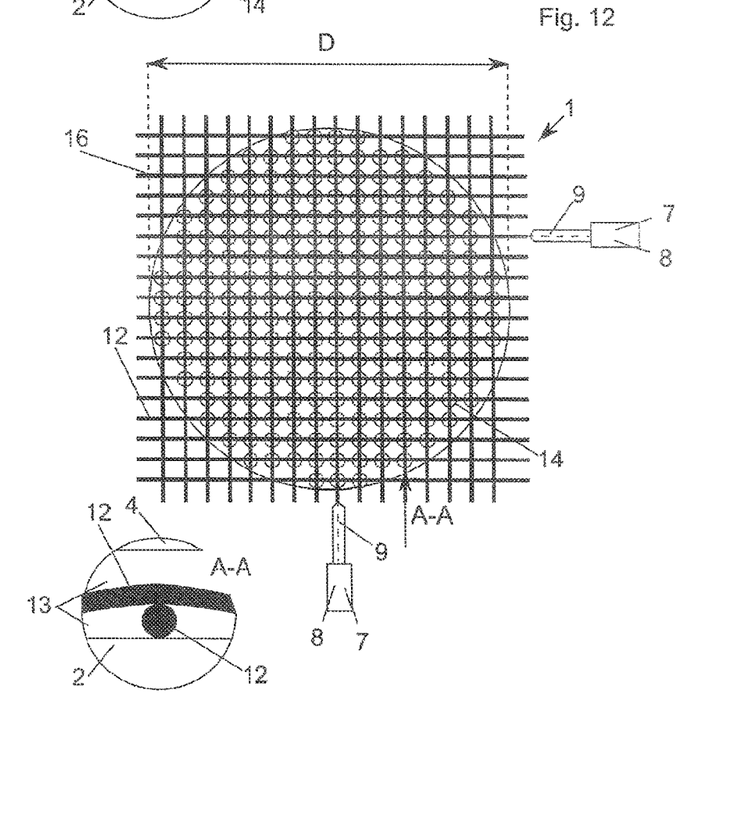
FIG. 12 shows a schematic plan view of a seventh embodiment of a measuring device.

In the further embodiment of the invention shown in FIG. 12 there are several optical fibers 12 in the measurement layer 3 in the form of a grating. The grating is preferably set up rectangularly, the respective optical fibers intersecting at a right angle.

Thus the optical fibers 12 at reference points (crossing points) mutually form pressure bodies for the optical fiber 12 which is crossing at the time. In this case there is a transmitter 7 either at the start and a receiver 8 at the end or a transmitter-receiver unit on one side.

The measurement of a signal change or a change of the optical properties of the signal under compressive stress takes place at the reference points (crossing points). At them there are two optical fibers 12 transversely to one another and on top of one another and they are in especially direct contact with one another. The compressive stress at the crossing point compresses the optical material of the optical fibers 12. The change of double refraction, the change in the index of refraction, the change of the density of the optical material or the change of the mode of the TEM wave can be determined accordingly.

All signals along the width and length of the rectangular grating of the optical fibers 12 are recorded and evaluated by the evaluation unit, as a result of which the determination of the origin of the change of the respective optical property and thus the conversion into the respective, localized pressure value are possible.

REFERENCE NUMBER LIST 1 measuring device
2 first substrate
3 measurement layer
3u peripheral edge
4 second substrate
5 first pressure body
6 second pressure body
7 transmitter
8, 8' receiver
9 signal
12 optical fiber
13 matrix
14 pressure elements
15 reflectors
D diameter
L partial section of the measurement system
t, t' thickness of the measurement layer Having described the invention, the following is claimed:

1. A measuring device for determining a pressure map before and/or during a bond process, the measuring device comprising:
a sensor comprising a first substrate, a second substrate, and a measurement layer by which the first substrate and the second substrate are permanently connected, the measurement layer being disposed between the first substrate and the second substrate, the measurement layer including an optical material having optical properties that are configured to change when exposed to pressure applied to the measurement layer, the sensor being disposed between a first pressure body and a second pressure body, the first pressure body being separated from the measurement layer by the first substrate, the second pressure body being separated from the measurement layer by the second substrate, the pressure bodies being configured to apply said pressure to the measurement layer,
a transmitter located on a peripheral edge of the measurement layer for emission of signals in the form of electromagnetic waves along a first signal route which runs through the measurement layer and at least one other signal route which runs through the measurement layer, the emitted signals being configured to change when exposed to changes in pressure applied by the pressure bodies to the measurement layer,
a receiver located on the peripheral edge of the measurement layer, the receiver being configured to receive the emitted signals of the first signal route and the at least one other signal route through the measurement layer and record the received signals, and
an evaluation unit configured to evaluate the received and recorded signals along the signal routes and form the pressure map by determining localized pressure values from the evaluated signals by reconstruction of the evaluated signals.

2. The measuring device as claimed in claim 1, wherein the measuring device is used in a wafer processing device.

3. The measuring device as claimed in claim 1, wherein the transmitter and/or the receiver are/is moved along the peripheral edge of the measurement layer.

4. The measuring device as claimed in claim 1, wherein the transmitter is one of a plurality of transmitters distributed on the peripheral edge of the measurement layer.

5. The measuring device as claimed in claim 4, wherein each of said transmitters emits several signal routes.

6. The measuring device as claimed in claim 1, wherein the receiver acquires optical properties of the signal.

7. The measuring device as claimed in claim 6, wherein the optical properties of the signal include one or more of the following properties:
double refraction, index of refraction, mode of signals shaped as transverse electromagnetic waves, transit time, and spectral coding.

8. The measuring device as claimed in claim 1, wherein the receiver is one of a plurality of receivers distributed on the peripheral edge of the measurement layer.

9. The measuring device as claimed in claim 8, wherein the transmitter is one of a plurality of transmitters distributed on the peripheral edge of the measurement layer, and
wherein said receivers are assigned to one of said transmitters at a time.

10. The measuring device as claimed in claim 8, wherein the transmitter is one of a plurality of transmitters distributed on the peripheral edge of the measurement layer, and
wherein two or more of said receivers are assigned to each of said transmitters.

11. The measuring device as claimed in claim 8, wherein each of said receivers is assigned to one single signal route at a time.

12. The measuring device as claimed in claim 11, wherein the transmitter is one of a plurality of transmitters distributed on the peripheral edge of the measurement layer, and
wherein each of said transmitters emits several signal routes.

13. The measuring device as claimed in claim 1, wherein said evaluation unit determines the localized pressure values by a transform for the reconstruction of the evaluated signals.

14. The measuring device as claimed in claim 13, wherein said transform is a Radon transform.

15. The measuring device as claimed in claim 1, wherein the first substrate is permanently cemented to the second substrate by the optical material.

16. The measuring device as claimed in claim 1, wherein the pressure is applied to the measurement layer only by the first pressure body and the second pressure body.

17. The measuring device as claimed in claim 1, wherein the measurement layer bonds the first substrate to the second substrate.

18. The measuring device as claimed in claim 1, wherein the sensor constitutes a wafer stack.

19. A method for determining a pressure map before and/or during a bond process, the method comprising:
- arranging a sensor of a measuring device between a first pressure body and a second pressure body, the sensor comprising a first substrate, a second substrate, and a measurement layer by which the first substrate and the second substrate are permanently connected, the measurement layer being disposed between the first substrate and the second substrate, the measurement layer including an optical material having optical properties that are configured to change when exposed to pressure applied to the measurement layer,
- applying said pressure to the measurement layer by the pressure bodies, the first pressure body being separated from the measurement layer by the first substrate, the second pressure body being separated from the measurement layer by the second substrate,
- emitting, using a transmitter of the measuring device, signals in the form of electromagnetic waves along a first signal route running through the measurement layer and at least one other signal route which runs through the measurement layer such that the emitted signals are changed when exposed to changes in pressure applied by the pressure bodies to the measurement layer, the transmitter being located on a peripheral edge of the measurement layer,
- receiving, using a receiver of the measuring device, the emitted signals of the first signal route and the at least one other signal route, the receiver being located on the peripheral edge of the measurement layer,
- recording, using the receiver, said received signals,
- evaluating, using an evaluation unit of the measuring device, the received and recorded signals along the signal routes, and
- forming, using the evaluation unit, the pressure map by determining localized pressure values from the evaluated signals by reconstruction of the evaluated signals.

20. The method as claimed in claim 19, wherein the first substrate is permanently connected to the second substrate by the optical material.

21. A measuring device for determining a pressure map before and/or during a bond process, the measuring device comprising:
- a measurement layer disposed between a first substrate and a second substrate, the measurement layer including an optical material permanently cementing the first substrate to the second substrate, the optical material having optical properties that are configured to change when exposed to pressure applied to the measurement layer, the sensor being disposed between a first pressure body and a second pressure body, the first pressure body being separated from the measurement layer by the first substrate, the second pressure body being separated from the measurement layer by the second substrate, the pressure bodies being configured to apply said pressure to the measurement layer,
- a transmitter located on a peripheral edge of the measurement layer for emission of signals in the form of electromagnetic waves along a first signal route which runs through the measurement layer and at least one other signal route which runs through the measurement layer, the emitted signals being configured to change when exposed to changes in pressure applied by the pressure bodies to the measurement layer,
- a receiver located on the peripheral edge of the measurement layer, the receiver being configured to receive the emitted signals of the first signal route and the at least one other signal route through the measurement layer and record the received signals, and
- an evaluation unit configured to evaluate the received and recorded signals along the signal routes and form the pressure map by determining localized pressure values from the evaluated signals by reconstruction of the evaluated signals.

* * * * *